(12) United States Patent
Swope et al.

(10) Patent No.: US 9,554,797 B2
(45) Date of Patent: Jan. 31, 2017

(54) TISSUE-ACQUISITION DEVICE AND METHOD

(71) Applicant: Boston Scientific Scimed, Inc., Maple Grove, MN (US)

(72) Inventors: Bretton Swope, San Francisco, CA (US); Tyler Grubb, Denver, CO (US); Daniel Balbierz, Redwood City, CA (US); Craig Purdy, Campbell, CA (US); David Cole, San Mateo, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 545 days.

(21) Appl. No.: 13/740,129

(22) Filed: Jan. 11, 2013

(65) Prior Publication Data

US 2013/0184723 A1  Jul. 18, 2013

Related U.S. Application Data

(60) Provisional application No. 61/586,657, filed on Jan. 13, 2012.

(51) Int. Cl.

| | | |
|---|---|---|
| *A61B 17/068* | (2006.01) | |
| *A61B 17/08* | (2006.01) | |
| *A61B 17/072* | (2006.01) | |
| *A61F 5/00* | (2006.01) | |
| *A61B 17/02* | (2006.01) | |
| *A61B 17/115* | (2006.01) | |
| *A61B 17/00* | (2006.01) | |
| *A61B 17/29* | (2006.01) | |
| *A61B 17/30* | (2006.01) | |

(52) U.S. Cl.
CPC ............ *A61B 17/08* (2013.01); *A61B 17/0686* (2013.01); *A61B 17/072* (2013.01); *A61F 5/0086* (2013.01); *A61B 17/0206* (2013.01); *A61B 17/0218* (2013.01); *A61B 17/115* (2013.01); *A61B 2017/00818* (2013.01); *A61B 2017/2927* (2013.01); *A61B 2017/306* (2013.01)

(58) Field of Classification Search
CPC ............ A61B 17/0206; A61B 17/0218; A61B 17/0686; A61B 17/072; A61B 17/08; A61B 17/115; A61B 2017/00818; A61B 2017/2927; A61B 2017/306
See application file for complete search history.

(56) References Cited

U.S. PATENT DOCUMENTS

| | | |
|---|---|---|
| 4,841,888 A | 6/1989 | Mills et al. |
| 5,685,840 A | 11/1997 | Schechter et al. |
| 6,558,400 B2 | 5/2003 | Deem et al. |
| 7,862,574 B2 | 1/2011 | Deem et al. |
| 2002/0082621 A1 | 6/2002 | Schurr et al. |
| 2003/0139752 A1 | 7/2003 | Pasricha et al. |
| 2009/0312602 A1* | 12/2009 | Sakamoto .......... A61B 17/0469 600/104 |
| 2011/0174864 A1 | 7/2011 | Cole et al. |

OTHER PUBLICATIONS

International Search Report issued Mar. 29, 2013 for International Appln. No. PCT/US2013/021291 filed Jan. 11, 2013.

* cited by examiner

*Primary Examiner* — Ashley Fishback
(74) *Attorney, Agent, or Firm* — Bookoff McAndrews, PLLC (57) ABSTRACT

Described herein is an improved device and method for acquiring, and optionally, fastening a tissue fold. The device has an improved configuration for forming a single, two-layer tissue fold.

29 Claims, 10 Drawing Sheets

TISSUE-ACQUISITION DEVICE AND METHOD

CROSS-REFERENCE TO RELATED APPLICATION

The present application is a non-provisional of U.S. Patent Application No. 61/586,657, filed on Jan. 13, 2012.

FIELD OF THE INVENTION

The present invention relates generally to the field of a device and method for acquiring, and optionally, fastening a tissue fold.

BACKGROUND OF THE INVENTION

One of the current methods of treating obesity is to reduce stomach volume by forming extended and/or multiple two-layer tissue folds in the stomach. Ideally, the method is carried so that up to one half or more of the original area of the stomach interior is sequestered in tissue folds, reducing both the volume of the stomach and area within the stomach that can interact with ingested food. This approach has the general advantages in treating obesity that (i) it is non-invasive in that it is carried out using an intra-oral stapling procedure; (ii) stomach volume can readily reduced by a desired amount, e.g., between 50-80 percent, according to the number and sizes of folds formed, (iii) the tissue folds may be formed in areas of the stomach, e.g., the fundus, that are especially susceptible to appetite control, and (iv) the procedure can be readily repaired or fine-tuned by simply by forming additional tissue folds as needed in one or more follow-up procedures.

Devices designed for treating obesity and/or gastroesophageal reflux disease (GERD) by forming stomach plications are known, e.g., U.S. Pat. Nos. 5,571,116, 5,887,594, 6,113,609, 6,159,146, and 6,592,596. Several U.S. patents, including U.S. Pat. No. 6,663,639, and related U.S. Pat. Nos. 6,494,888, 6,773,441 and 7,736,373 disclose endoscopic methods of reconfiguring the stomach by manipulating two or more separate tissue folds. Similar methods for reconfiguring the stomach by bringing together two or more tissue folds are disclosed in U.S. Pat. No. 6,558,400, and related U.S. Pat. Nos. 7,288,099, 7,288,101, 7,510,559, U.S. Pat. Nos. 7,503,922, and 7,862,574. U.S. Pat. No. 7,175,638 also discloses and claims reconfiguring the stomach by forming pairs of tissue folds, i.e., one or more four-layer folds.

Co-owned U.S. Pat. Nos. 7,708,181, 7,721,932, 7,909,219, 7,909,222, 7,909,223, 7,913,892, 7,922,062, 7,934,631, and 8,020,741 disclose a device for forming and stapling tissue folds in the stomach. The device includes staple and anvil members that are operable to move toward and away from one another along a first axis, and arm assemblies connecting the two members and that expand outwardly, along a second axis substantially perpendicular to the first axis, as the proximal and distal members move toward one another to a tissue-capture position. The confronting faces of the two members and the arm assemblies connecting them define a tissue-capture chamber that is covered by the by a flexible-membrane sleeve having an opening through which tissue is drawn when the opening is placed against tissue and a vacuum is applied to the chamber. The device has a low-profile in a relaxed mode, for intra-oral insertion, and expands outwardly, during operation, to allow a relatively large two-layer tissue fold to be drawn into the chamber. Once a tissue fold is captured in the chamber, the device may be operated to place a ring of staples through the fold and, optionally, to form a cutout in the tissue fold within the ring of staples. One limitation of the device that has been observed, however, is that more than two layers of tissue may be drawn into the chamber, during vacuum uptake, and/or that a portion of the flexible-membrane sleeve that surround the sleeve opening may itself be drawn into the chamber, and stapled to the tissue fold.

It would thus be desirable to provide an improved device for forming a tissue fold, e.g., within the stomach, which has the advantages of the above-described device, but overcomes the current limitations in tissue uptake.

SUMMARY OF THE INVENTION

In one aspect, the invention includes an improvement in a device for forming a tissue fold composed of two tissue layers, by drawing tissue into a tissue chamber in the device through an opening in a flexible-membrane sleeve that covers the tissue chamber, upon the application of a vacuum to the chamber when the sleeve opening is placed against tissue. The improvement comprises a sleeve opening in the form of an elongate slit having a gap dimensioned to restrict intake through the slit of additional tissue layers, once the two tissue layers of the tissue fold have been drawn into the tissue chamber through the slit.

The gap in the slit may be dimensioned to maintain the two layers of a tissue fold in contact with one another as they are being drawn into the tissue chamber through the slit. The gap, in the relaxed state of the sleeve, may be between 10 and 200 mils.

The sleeve may be formed of silicon having a durometer hardness of between 25-35 Shore A and a membrane thickness of between 20-50 mils. The sleeve may have a reinforcing lip about the slit to aid in supporting the slit as tissue is being drawn through the slit under a vacuum.

The device may operate to stretch the slit in a lengthwise direction, during application of vacuum to the chamber, and the gap in the slit may remain dimensioned to restrict intake through the slit of additional tissue layers, once the two tissue layers of the tissue fold have been drawn into the tissue chamber through the slit, as the slit is stretched in a lengthwise direction. The slit may have a lengthwise dimension, in a relaxed state, of between about 10-15 mm, and in a fully stretch state, between 25-50 mm.

The improved device may further include a reservoir connecting the tissue chamber in the device to a vacuum source, for modulating the rate at which vacuum is applied to the device chamber from the vacuum source.

In one general embodiment, the tissue chamber in the device is defined by (i) confronting faces of proximal and distal members that are operable to move toward and away from one another along a first axis, (ii) arm assemblies connecting the two members and that expand outwardly, along a second axis substantially perpendicular to the first axis, as the proximal and distal members move toward one another to a tissue-capture position, and (iii) the flexible-membrane sleeve covering at least portions of said two members and having an intermediate portion covering said chamber. Here the sleeve slit is oriented lengthwise in the direction of said second axis, such that movement of the arm assemblies outwardly, as the two members are moved toward one another, acts to stretch said slit in a lengthwise direction.

In this embodiment, the sleeve may include reinforcing plates disposed on either side of said slit and extending axially in the direction of the movement of the associated proximal or distal members, and being supported thereon, to resist forces on the slit in the direction of tissue intake. The interior surface of said sleeve may have one or more slots extending axially along the direction of travel of the two members, to maintain a vacuum connection within the chamber as a tissue fold presses against said interior surface during acquisition of a tissue fold. At least one of the arm assemblies may include an elbow that defines a nubbin slot, and the interior surface of the sleeve may include at least one nubbin that is received in an associated nubbin slot, when the sleeve is properly positioned on proximal and distal members of the device, to retain the sleeve in place when the assembly arms are expanded and the sleeve is stretched along the second axis. This embodiment of the device may include a staple cartridge and staple driver in one housing, a staple anvil in the other housing, and a hydraulic line by which the staple cartridge can be activated, when a tissue fold is captured in the device, to fasten the fold with one or more staples.

In another aspect, the invention includes an improvement in a method for forming a tissue fold composed of two tissue layers, by drawing tissue into a tissue chamber through an opening in a flexible-membrane sleeve, upon the application of a vacuum to the chamber when the opening placed against tissue. The improvement includes the steps of (a) placing against the tissue, a flexible-membrane sleeve whose opening is an elongate slit having a gap dimensioned to restrict intake through the slit of additional tissue layers; once the two tissue layers of the tissue fold have been drawn into the tissue chamber through the slit; and (b) applying to the chamber, a vacuum that increases in a controlled manner as tissue is being drawn into the chamber.

The sleeve's elongate slit that is positioned against the tissue in step (a) may be dimensioned to maintain the layers of a tissue fold in contact with one another as they are being drawn into the tissue chamber through the slit. The slit may have a width, in the relaxed state of the sleeve, of between 20 to 125 mils.

The improvement method may further include during applying step (b), stretching the slit in a lengthwise direction, and step (b) may be carried out such that a maximum vacuum in the vacuum chamber is reached after the slit has been fully stretched. Step (b) may be carried out by applying a vacuum to a reservoir bottle that is connected to the tissue chamber.

Also disclosed is an apparatus for forming a tissue fold composed of two tissue layers, comprising (a) a device having a tissue chamber covered by a flexible-membrane sleeve, the sleeve having an elongate slit with a gap dimensioned to restrict intake through the slit of additional tissue layers, once the two tissue layers of the tissue fold have been drawn into the tissue chamber through the slit, under a vacuum applied to the chamber; (b) a vacuum source for applying vacuum to said chamber; and (c) a controller operatively connected to said vacuum source for controlling the rate at which vacuum is applied to said chamber, to control the rate at which tissue is drawn into said chamber.

As above, the gap in the slit may be dimensioned to maintain the two layers of a tissue fold in contact with one another as they are being drawn into the tissue chamber through the slit, and in the relaxed state of the sleeve, may be between 40 and 125 mils.

The controller in the apparatus may be a reservoir bottle operatively connecting the vacuum source to the vacuum chamber.

The device may operate to stretch the slit lengthwise as the controller is controlling the rate of vacuum being formed in said chamber.

In one general embodiment, the device includes a tissue chamber defined by (i) confronting faces of proximal and distal members that are operable to move toward and away from one another along a first axis, (ii) arm assemblies connecting the two members and that expand outwardly, along a second axis substantially perpendicular to the first axis, as the proximal and distal members move toward one another to a tissue-capture position, and (iii) the flexible-membrane sleeve covering at least portions of said two members and having an intermediate portion covering said chamber, and wherein the slit in the sleeve is oriented lengthwise in the direction of said second axis, such that movement of the arm assemblies outwardly, as the two members are moved toward one another, acts to stretch said slit in a lengthwise direction.

The sleeve in this embodiment may include reinforcing plates disposed on either side of said slit and extending axially in the direction of the movement of the associated proximal or distal members, and being supported thereon, to resist forces on the slit in the direction of tissue intake. The interior surface of the sleeve may have one or more slots extending axially along the direction of travel of the two members, to maintain a vacuum connection within the chamber as a tissue fold presses against said interior surface during acquisition of a tissue fold. At least one arm assembly may include an elbow that defines a nubbin slot, and the interior surface of the sleeve may include at least one nubbin that is received in an associated nubbin slot, when the sleeve is properly positioned on proximal and distal members of the device, to retain the sleeve in place when the assembly arms are expanded and the sleeve is stretched along the second axis.

The device may include a staple cartridge and staple driver in one housing, a staple anvil in the other housing, and a hydraulic line by which the staple cartridge can be activated, when a tissue fold is captured in the device, to fasten the fold with one or more staples.

The controller may be a reservoir bottle operatively connecting the vacuum source to the vacuum chamber.

These and other objects and features of the invention will become more fully apparent when the following detailed description of the invention is read in conjunction with the accompanying drawings.

DETAILED DESCRIPTION OF THE DRAWINGS

The present application describes an improvement in an endoscopic device for forming and, optionally, fastening a tissue folds. In preferred embodiments, the device may be passed transorally into the stomach and used to plicate stomach tissue.

Figure 1A:
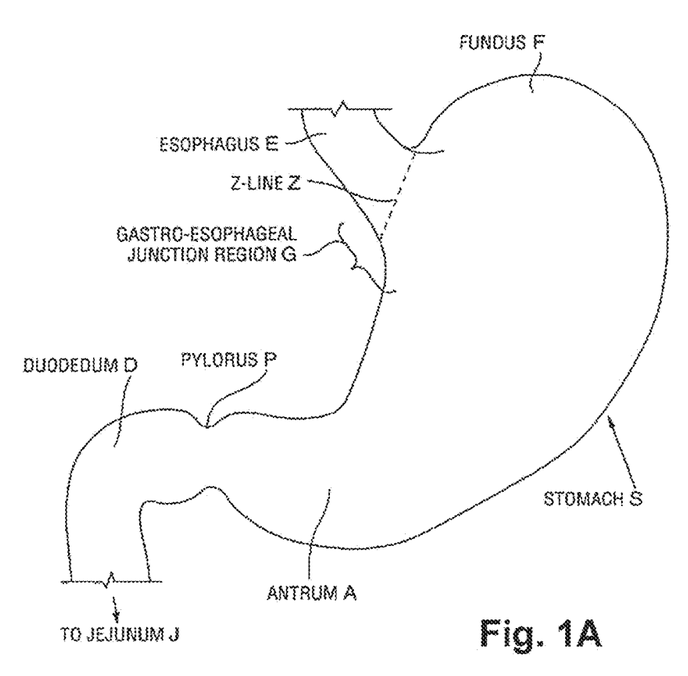
FIG. 1A is a schematic illustration of a human stomach and a portion of the small intestine, as known in the prior art.

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S. Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Figure 1B:
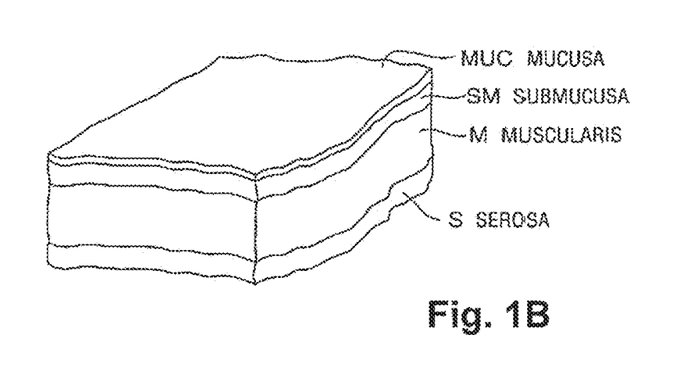
FIG. 1B is a cross-sectional perspective view of a portion of a stomach wall, illustrating the layers of tissue forming the wall, also as known in the prior art.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

In the disclosed embodiments of the present invention, the improved device is introduced into the stomach intra-orally, via the esophagus. Typically the device is equipped with an endoscope that allows the physician to view the interior region of the stomach, and guiding structure by which the device can be positioned at a desired target location within the stomach, i.e., the region at which the device will form a tissue fold. When the device is placed against a tissue region, and vacuum is applied, a portion of the interior stomach wall is drawn inwardly into the device, forming a two-layer fold or plication that brings sections of serosal tissue on the exterior of the stomach into contact with one another. The disclosed device allows the opposed sections of tissue to be pressed into contact with one another, and, optionally, delivers fasteners that will hold the tissue sections together until at least such time as serosal bonds form between them. Each of these steps may be performed wholly from the inside of the stomach and thus can eliminate the need for any surgical or laparoscopic intervention. After one or more plications is formed, medical devices (including, but not limited to any of the types listed above) may be coupled to the plication(s) for retention within the stomach.

The disclosed embodiments may include, in addition to a fastener for fastening tissue folds formed in the device, a feature that forms a hole or cut in a plication using the fastener-applying device. This hole or cut might be formed so that a portion of a medical implant may be passed through or linked to the hole/cut, or it may be formed so as to provoke a healing response that will contribute to the strength of the resulting tissue bond.

In the description of the embodiments given below, the fasteners in the device are described as being staplers, and exemplary methods are given with respect to the formation of stapled plications in stomach tissue. It should be understood, however, that the fastener embodiments described herein include features having equal applicability for applying other types of fasteners, and for applying staples or other fasteners for purposes other than formation of plications. More specifically, the term "staple" is used herein to designate any type of fastener that (i) can be pushed through tissue, and (ii) has one or more leg members that when forced against an anvil are crimped to secure the fastener to the tissue and hold tissue fastened tissue fold together. The disclosed embodiments and methods will also find use in parts of the body outside the GI system. Additionally, although the disclosed embodiment features circular stapling and cutting of a concentric hole, modifications are conceivable in which linear stapling can be accomplished, as well as circular or linear stapling without cutting.

Figure 2:
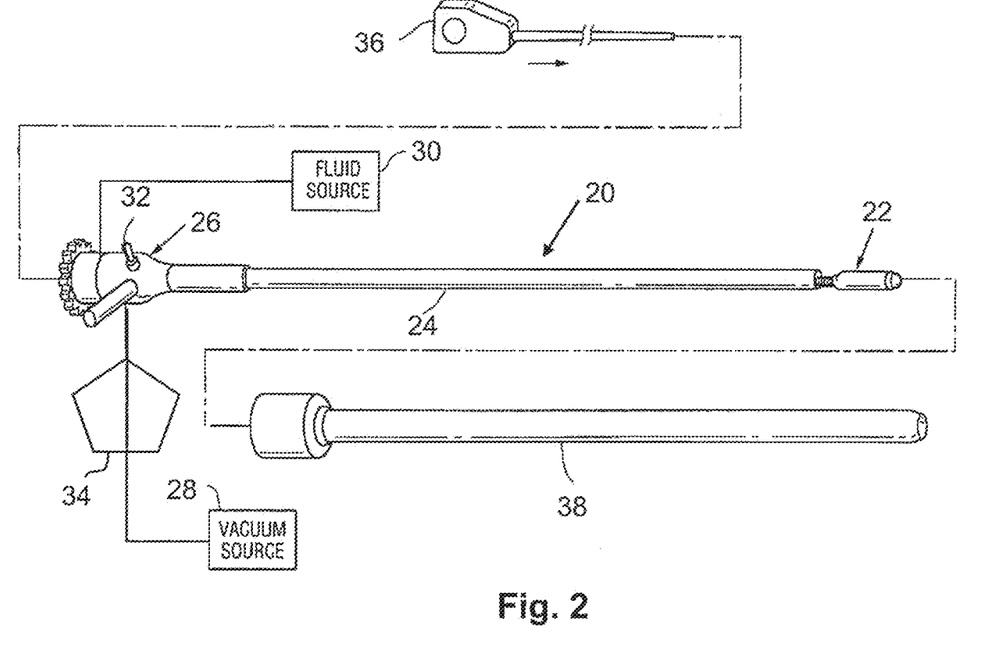
FIG. 2 illustrates an endoscopic tissue-fold and stapling system and device constructed in accordance with an embodiment of the invention.

FIG. 2 illustrates one embodiment of a system or instrument 20 which includes the improved tissue-capture device, indicated at 22, for forming a two-layer tissue fold or plication. The device carried at the distal end of a flexible shaft 24. A handle 26 at the proximal end of the shaft controls articulation of the device and actuation of the tissue acquisition, tissue compression, and, optionally, stapling the acquired tissue fold and or forming a hole in the fold. Vacuum and fluid sources 28, 30 in the system are fluidly coupled to handle 26 for use in tissue acquisition, compression and stapling as discussed below. The vacuum source may be the "house vacuum" accessible through a coupling on the wall of the operating room, or an auxiliary suction pump. The system may include a switch 32 allowing the user to control airflow between the vacuum source and stapler. Fluid source 30 may be a single source of drive fluid (e.g. water, saline, oil, gas) or multiple sources, but in each case the fluid source preferably includes two actuators separately used to control flow into each of two hydraulic lines (one for tissue compression and one for stapling). Also shown is a reservoir tank 34 connecting the vacuum source to the handle, for controlling the rate at which vacuum is applied to the tissue-acquisition device, as will be described below. An endoscope 36 in the system is insertable through a lumen in the shaft, and permits visualization of the plication procedure. The system may optionally include an overtube, such an endoscopic guide tube 38, having a lumen for receiving the shaft and attached device 22.

Figure 3A:
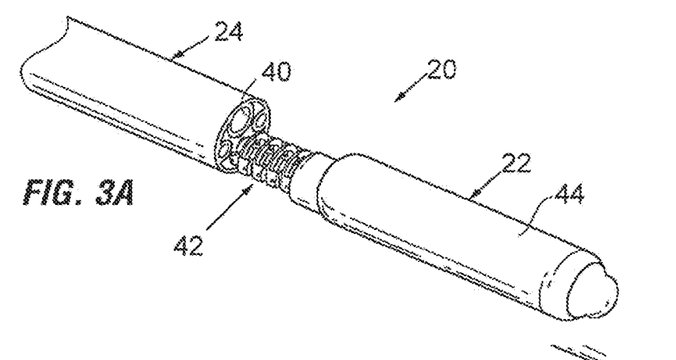
FIGS. 3A-3C are perspective views showing the tissue-fold and stapling device of the stapling system of FIG. 2 in three different positions.
Figure 3B:
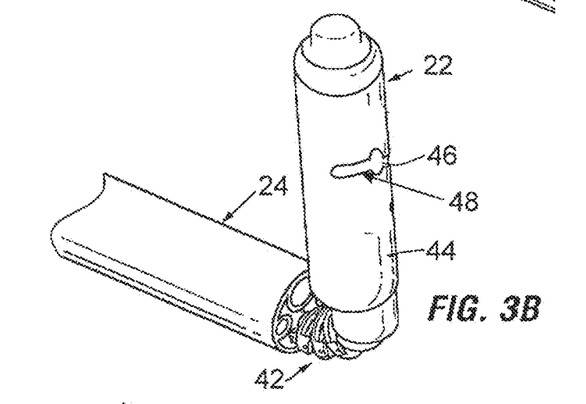
Figure 3C:
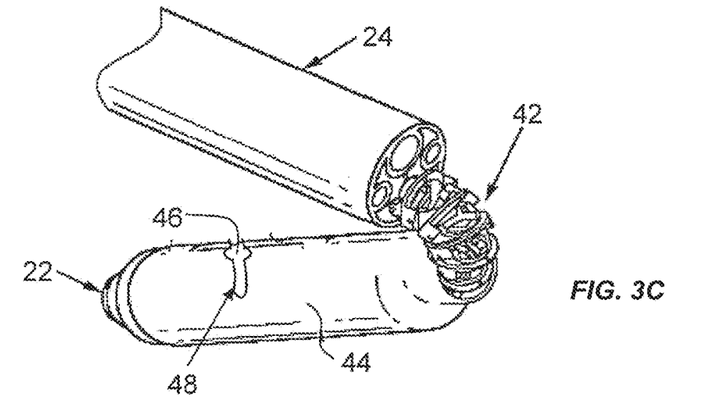

FIGS. 3A-3C show the distal end of the system 20, showing the connection of device 22 to the shafts distal end 40 through a multiple-link articulation arm 42. The position of arm 42 is controlled by the user at the handle, e.g., through conventional cable controls, for placing the tissue-acquisition device at selected positions and orientation with respect to the distal end of the shaft, illustrated in FIGS. 3A-3C.

With continued reference to FIGS. 3A-3C, device 22 includes a flexible-membrane covering 44 which covers the mechanical, tissue-capture elements of the device that are described below. The covering and certain mechanical elements that it covers form a vacuum chamber 46 in the device. A lateral slit 48 formed in the membrane provides an opening through which tissue is drawn into the chamber during operation. In the embodiment shown, covering 44 is sleeve or sock, and is referred to below as sleeve 44. In the embodiment detailed below in Section C, sleeve 44 is formed of silicone or other elastic, biocompatible material, and at least a central portion of the sleeve is sufficiently transparent to allow the user to view the interior of the tissue chamber during operation, to confirm (via endoscopic observation) that an appropriate volume of tissue has been acquired.

A. Tissue-Acquisition Device

One exemplary tissue-acquisition device 22 in the invention has the mechanical components and operation illustrated in FIGS. 4A-4C and FIG. 5. For purposes of description in this section, device 22 will be described with respect to its mechanical elements and to the operation of those elements illustrated in these figures, it being understood that the device also includes sleeve 44 which covers the mechanical elements of the device.

Figure 4A:
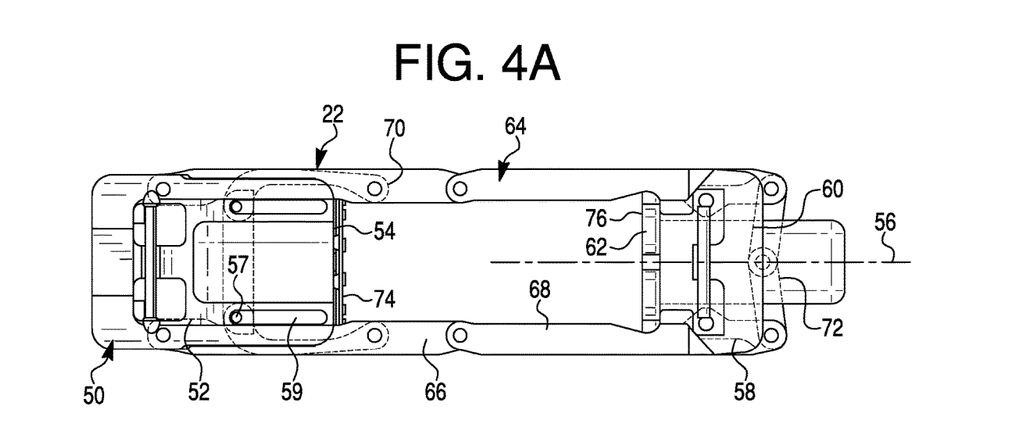
FIGS. 4A-4C are top plan views of the tissue-capture and stapling device FIG. 3, showing the device in its low-profile condition (4A), during travel of the staple and anvil members toward a tissue-capture condition (4B), and the device in its tissue-capture condition (4C)
Figure 4B:
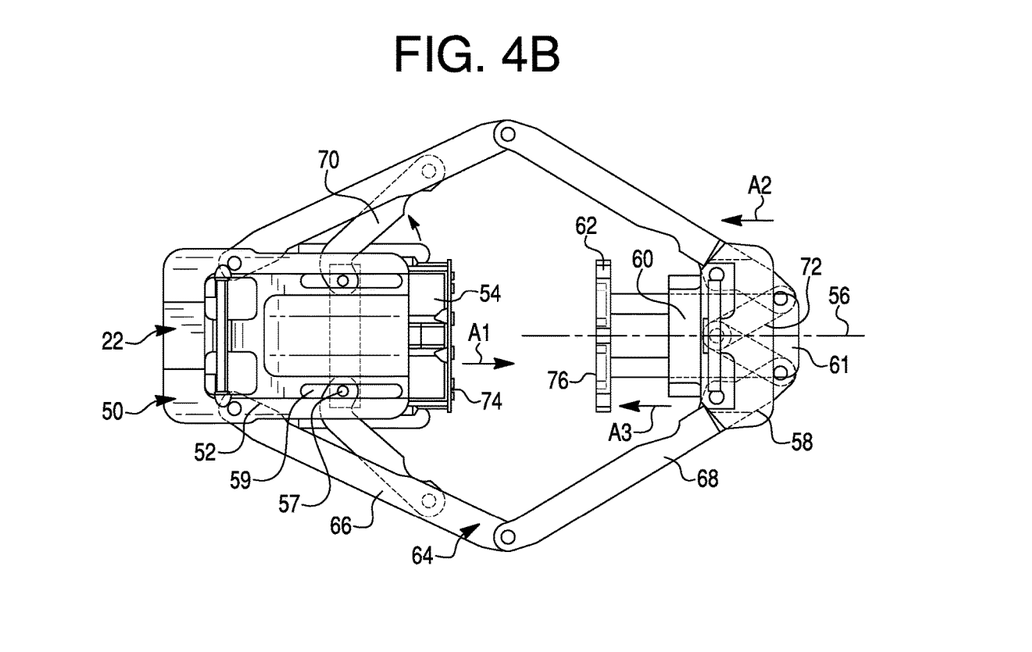
Figure 4C:
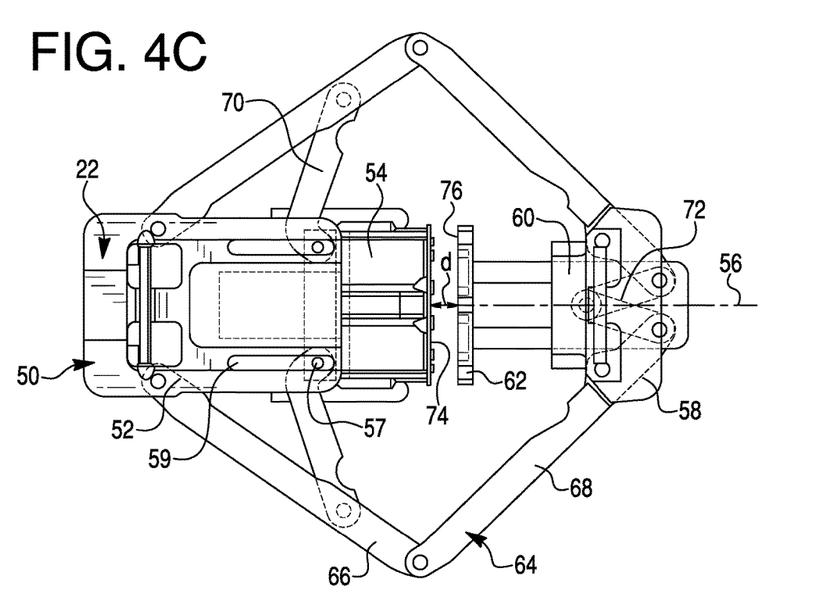

Device 22 is designed to have a minimum profile, shown in FIG. 4A, during insertion to the plication site; and designed to expand to the progressively larger profiles seen in FIGS. 4B and 4C during a tissue-acquisition operation.

Considering now the mechanical elements of device 22, a first or proximal member 50 includes a housing 52 and a stapler 54 that moves within the housing along an axis 56 extending in a horizontal direction in the figures. The extent of travel of the stapler within the housing is limited by a pair of pins 57 that travel within slots 59 formed in the housing, as can be appreciated from the positions of the pins in FIGS. 4A and 4C. A second or distal member 58 includes a housing 60 and an anvil 62 that moves with its associated housing also along axis 56. The two members are connected by a pair of arm assemblies 64 for movement toward and away from one another, along axis 56, between the low-profile condition shown in FIG. 4A and the fully expanded condition shown in FIG. 4C. Each arm assembly has proximal and distal arms 66, 68, respectively, that are pivotally joined to one another at their confronting ends, forming elbows in the assemblies, and are pivotally joined at their opposite ends to the associated member 50, 58, respectively.

Figure 5:
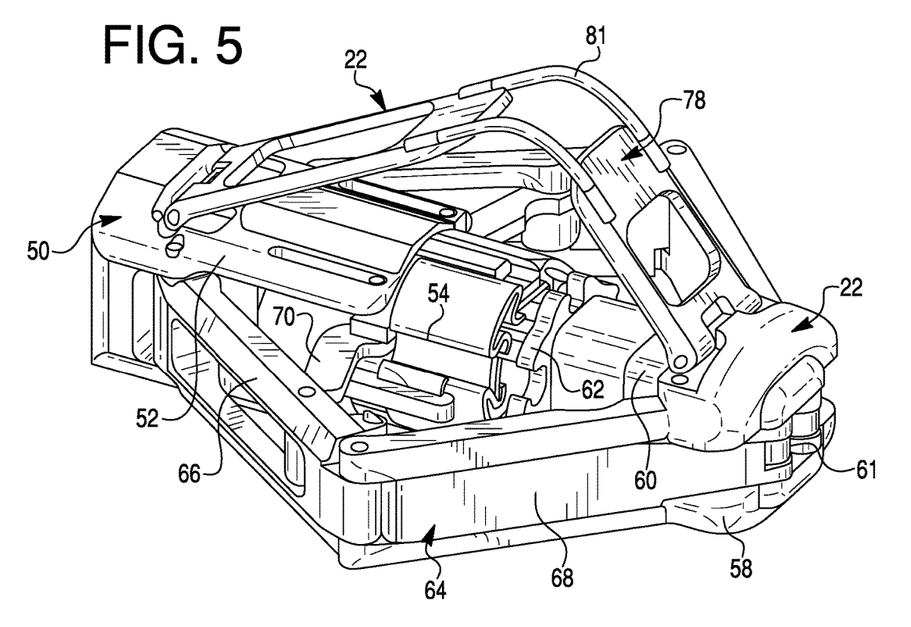
FIG. 5 is a perspective view of the device in its FIG. 4C condition, showing the positions of the arm assemblies and membrane raiser in the tissue-capture condition.

A pair of spreader arms 70 are anchored within housing 52 through pins 57, and pivotally attached to associated assembly arms 66 at the opposite ends of the spreader arms. As can be appreciated from the figures, movement of stapler 54 within its housing to the right in the figures, with corresponding travel of pins 57 within slots 59, acts to push spreader arms 70 outwardly, causing arms 66, 68 to spread outwardly and draw the two housings toward one another. At the same time, outward movement of arms 68 acts to move anvil 62 within its housing, toward the left in the figures, through a scissor-arm mechanism 72 connecting the distal ends of arms 68 to the anvil. Device 22 also has a flexible lifter arm 78 whose opposite ends are pivotally joined to the proximal and distal members, as seen in FIG. 5. The lifter arm functions to expand the cross-sectional area of the chamber in conjunction with the expansion of the two arm assembles during operation of the device, as can be appreciated from FIG. 5. In an exemplary embodiment, the vacuum chamber 46 in the device, which is defined by the arm assemblies and spreader arm, has a cross-sectional area of about 0.7-0.8 cm$^2$ in the low-profile condition shown in FIG. 4A, and a maximum cross-sectional area of 7-8 cm$^2$ in the fully expanded condition shown in FIG. 4C.

Actuation of the device is by compressed fluid supplied to a piston within housing 50 (not shown). This causes stapler 54 to move to the right in the figures relative to housing 50, as seen in FIGS. 4B and 4C, in turn causing the two spreader arms in the device to pivot away from one another, and forcing the two arm assemblies toward their expanded positions shown sequentially in FIGS. 4B and 4C. That is, actuation of the driving piston in the device causes the following sequence of events: (1) movement of the stapler within its housing along axis 56 toward the right in the figures, indicated by arrow A1 in FIG. 4B, (2) movement of the spreader arms and pivotally attached arm assemblies outwardly, away from axis 56, (3) movement of the two housings toward one another along axis 56, indicated by arrow A2 in FIG. 4B, (4) expansion of the spreader arm, and (5) movement of the anvil within its housing to the left along axis 56, indicated by arrow A3 in FIG. 4B. When the device has executed its full extent of travel, that is, when pins 57 reach their stop positions within slots 59, the stapler and anvil are positioned at a tissue-capture condition, seen in FIG. 4C, at which the confronting faces of the stapler and anvil, indicated at 74, 76, respectively, are separated by a distance d. In an exemplary embodiment, distance d is selected between 0.06-0.07 inches (e.g. for use with staples having legs of 5.5 mm length) or 0.105 to 0.115 inches for 6.5 mm leg length staples. Application of additional pressure into the hydraulic circuit will not compress the tissue any further.

Figure 6A:
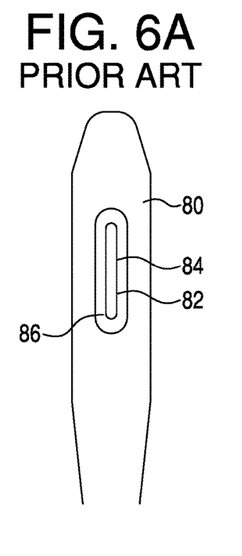
FIGS. 6A-6C show a flexible-membrane sleeve constructed in accordance with the prior art (6A), and the same sleeve carried on a tissue-capture and stapling device in a relaxed (6B) and stretched (6C) condition.

As will be appreciated from Section D below, a vacuum applied to the device at the same time or shortly after the mechanical elements are being driven toward their fully expanded condition, acts to draw tissue into the chamber. As it is being drawn in, the tissue fold expands outwardly, tending to fill the expanding cross section of the chamber, until the tissue chamber is fully expanded and the tissue fold is captured between the confronting faces of the stapler and anvil. Details of the device just described, and its mode or operation, are given in co-owned U.S. Pat. Nos. 8,020,741, 7,922,062, 7,913,892, 7,909,233, 7,909,222, and 7,909, 219, all of which are incorporated herein in their entirety. In particular, these patents describe in detail how staples are and ejected through a tissue B. Prior-Art Flexible-Membrane Sleeve FIGS. 6A-6C show a prior-art flexible-membrane sleeve 80 of the type disclosed in the above-cited co-owned patents, where FIG. 6A shows the detached sleeve, and FIGS. 6B and 6C show the sleeve carried on a tissue-acquisition device of the type described above and shown in partially expanded (FIG. 6B) and fully expanded (FIG. 6C) conditions. The sleeve has a vertically-disposed rectangular opening 82 whose midpoint 84 is close to the capture position of a two-layer fold in the tissue chamber between stapler and anvil faces 74, 76 seen in FIG. 4C. The opening has a thickened lip or ridge 86 about its periphery to serve as a reinforcing structure. The sleeve is dimensioned to cover the mechanical elements of the tissue-capture device, forming a tissue-capture chamber therewith, and is formed, for example, of silicone or other elastic, biocompatible material, and at least a central portion of the membrane is sufficiently transparent to allow view the interior of the tissue chamber during operation.

Figure 6B:
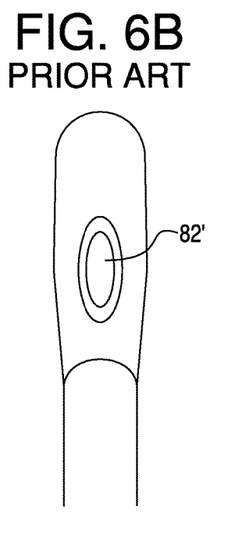
Figure 6C:
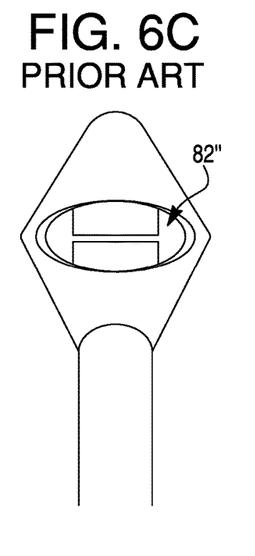

FIG. 6B shows the condition of the sleeve as the device first begins to move toward its expanded, tissue-capture position. As the arm assemblies and spreader arm in the device begin moving outwardly and upwardly, respectively, the opening is widened laterally, producing a vertically oriented, ovoid opening 82'. With continued movement of the device toward its tissue-capture position, the opening is stretched progressively toward the enlarged, horizontally disposed ovoid opening 82" seen in FIG. 6C. The fully stretched opening has roughly the same height dimension as opening 82 in its relaxed condition (FIG. 6A), and a horizontal dimension that typically about 70-90% the distance between the elbows of the fully extended arm assemblies in FIG. 4C. Typical dimensions of the opening in its fully stretch condition are 10-15 mm in height (vertical dimension in the figures) and between 25-40 mm in width (horizontal dimension in the figures).

Figure 7A:
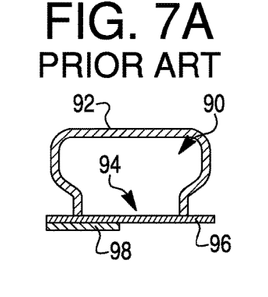
FIGS. 7A-7F illustrate tissue intake into a tissue chamber having a large tissue window where a secondary layer of tissue does not span the entire window (7A-7C); and tissue intake into a tissue chamber having a large tissue window where a secondary layer of tissue spans the entire window (7D-7F)
Figure 7B:
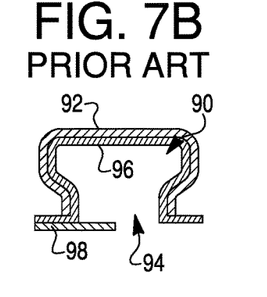
Figure 7C:
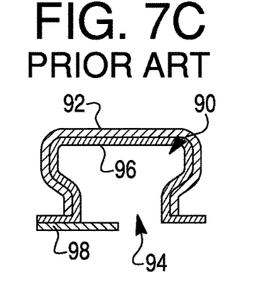

FIGS. 7A-7F illustrate schematically how the opening in the prior art sleeve can lead to unwanted tissue-acquisition effects. The figures show a cross section of a tissue intake chamber 90 in its expanded form, taken along a vertical section line in FIG. 6C, and defined by a outer sleeve 92 having a fully stretched opening 94 that corresponds to the maximum vertical dimension of opening 88 in FIG. 6C, e.g., between 10-15 mm. In FIG. 7A, the opening is positioned against a single layer 96 of tissue, e.g., stomach tissue, which itself is in contact with a second layer 98 of tissue disposed over a portion of the opening. The second layer may represent, for example, the wall of an organ or other tissue that is in contact with the outer wall of the stomach over a portion of the sleeve opening in the figures. When a vacuum is applied to the chamber, layer 96 is drawn into and against the walls of the chamber as shown in FIG. 7B. However, since tissue layer 98 doesn't form a complete seal around the opening, no pressure differential develops between the opening and the second layer, and there is little tendency of the second layer to be drawn into the chamber.

Figure 7D:
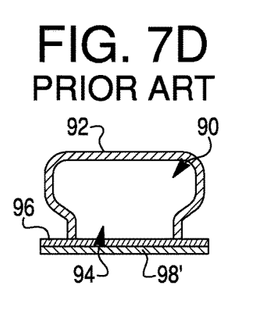
Figure 7E:
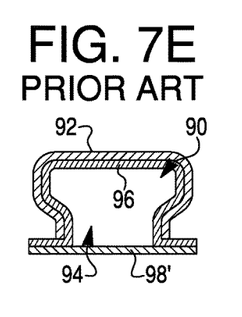
Figure 7F:
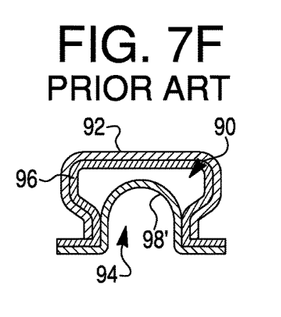

However, when a second layer 98' underlies tissue layer 96 over the entire area of the opening, as shown in FIG. 7D, drawing the target tissue layer into the chamber under a vacuum, as shown in FIG. 7E, produces a pressure differential across tissue layer 98' that acts to draw the second layer into chamber, as illustrated in FIG. 7F. The tissue chamber now contains two tissue folds, and applying a staple or other fastener across the folds can lead to fastening at least a portion of the second, lower fold to the two-layer inner fold. In the case of a stomach plication, this would result is a plicated portion of the stomach being attached to tissue external to the stomach.

Although not shown in these figures, the force of tissue against the sides of the opening during tissue acquisition can also deform portions of the sleeve opening itself into the chamber, with the danger that portions of the sleeve will be become stapled to the tissue fold. Both of the problems noted above have the potential to produce serious complications to a patient undergoing plication treatment for stomach reduction.

C. Improved Flexible-Membrane Sleeve

Figure 8A:
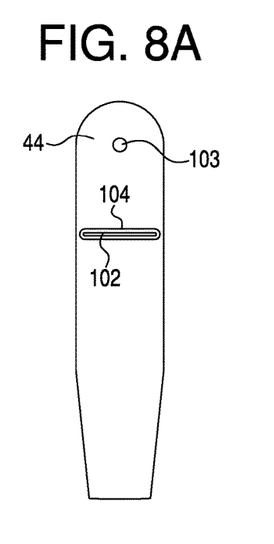
FIGS. 8A-8C show a flexible-membrane sleeve constructed in accordance with the present invention (8A), and the same sleeve carried on a tissue-capture and stapling device in a relaxed (8B) and stretched (8C) condition.
Figure 8B:
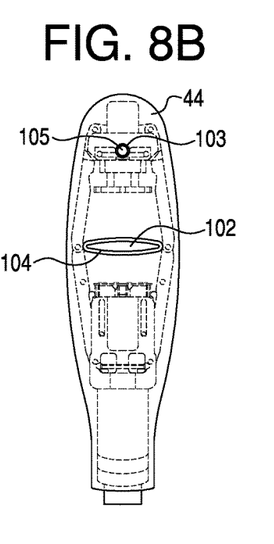
Figure 8C:
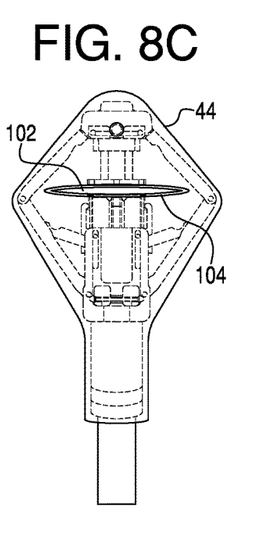

The improved flexible-membrane sleeve of the invention is shown at 44 in FIGS. 8A-8C, where FIG. 8A shows the detached sleeve, and FIGS. 8B and 8C show the sleeve carried on the plication device described above and shown in partially expanded (FIG. 8B) and fully expanded (FIG. 8C) conditions, similar to FIGS. 6A-6C. As will be discussed more fully below, the sleeve opening, through which tissue is drawn in tissue acquisition, is an elongate, horizontally extending slit 102 corresponding to slit 48 in FIGS. 3B and 3C, and having a gap dimensioned to restrict intake through the slit of additional tissue layers, once the two tissue layers of the tissue fold have been drawn into the tissue chamber through the slit. In an exemplary embodiment, the slit width (gap) in the relaxed condition of the sleeve shown in FIG. 8A is between 20 and 125 mils, typically about 30-50 mils, and the slit length in the relaxed condition is between about 0.5 to 0.8 includes, e.g., 12-19 mm. The slit has a circumferential lip or ridge 104 that helps the opening hold its shape during expansion and tissue acquisition. Also shown in FIG. 8A is a hole 103 located distal to the slit for engaging a mushroom-shaped button 105 in the anvil member in the device (FIG. 8B), to help anchor the sleeve on the device, along with other sleeve-anchoring structures described below.

FIG. 8B shows the condition of the slit as the tissue-acquisition in the early phase of tissue chamber expansion, analogous to the device in FIG. 6B. As the slit is stretched outwardly along its length, the width expands only slightly, retaining a relatively narrow gap through which tissue is drawn during a tissue-acquisition operation. Similarly, when the device is in its fully expanded state in FIG. 8C, the slit gap is still relatively narrow, even though the slit length has been expanded to 2-3 times its relaxed state. In particular, the slit width is such that, even as the slit is being expanded and is fully expanded, the slit gap is dimensioned to maintain the two layers of a tissue fold in contact with one another as they are being drawn into the tissue chamber through the slit.

Figure 9A:
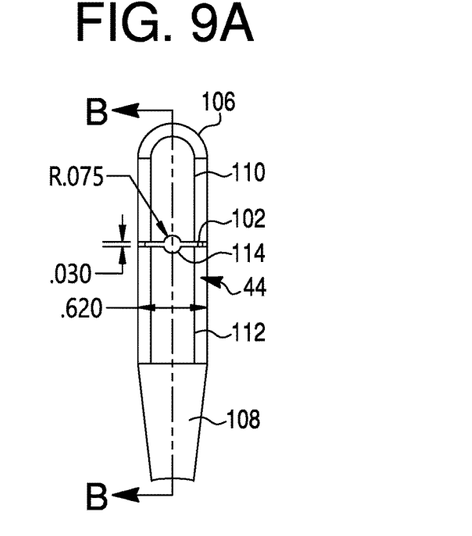
FIG. 9A shows features of the flexible-membrane sleeve in FIG. 8A.

The construction of sleeve 44 is detailed in FIGS. 9A, 9B, 10A, and 10B. The sleeve is shown in exterior, head-on view in FIG. 9A, showing its sock-like construction having a closed, rounded distal end 106, an open, tapered proximal end section 108, and horizontal slit 102 midway between distal and proximal sleeve sections 110, 112, respectively. The vertical dimensions of the sleeve exemplified in the figures are approximately 1.1 inches for each of sections 108, 110, and 112. The sleeve is attached to device 22, by pulling the sleeve over the device's distal end, until the sleeve's rounded distal end is positioned firmly against the distal end of the device, and the proximal tapered section of the sleeve covers at least a portion of the articulation arm 42 connecting device 22 to shaft 24. When so positioned, slit 102 is aligned with the elbows of the two arm assemblies in the device, and distal and proximal sections 110, 112 of the sleeve cover the distal and proximal regions of the chamber, respectively.

As seen in FIG. 9A, slit 102 has a central enlargement 114 that provides a point of initial tissue intake when vacuum is applied to the tissue chamber during operation. As such, the enlargement helps ensure that the tissue fold drawn into the chamber will be relatively evenly distributed from one side of the chamber to the other. The enlargement has a radius, in the embodiment shown, of about 75 mils.

Figure 9B:
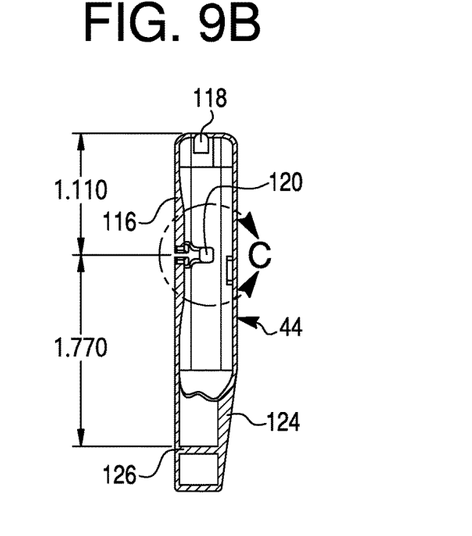
FIG. 9B shows the sleeve viewed along cross-sectional line B-B in FIG. 9A.

FIG. 9B is a sectional view of sleeve 44 taken along section line B-B in FIG. 9A. The figure shows a front plate 116 having a maximum thickness on either side of the slit, and tapering in thickness on moving away from the slit distally and proximally. A typical maximum thickness in plate 116 is 90 mils, and the minimum thickness at its distal and proximal ends is about 0.25 mils, corresponding to the sleeve thickness in regions where the sleeve has not been reinforced. The plate provides lateral support on either side of slit 102, to resist inward forces on the slit from tissue being drawn through the slit, i.e., forces that would otherwise cause the portions of the sleeve on either side of the slit to be drawn into the tissue chamber.

Figure 10A:
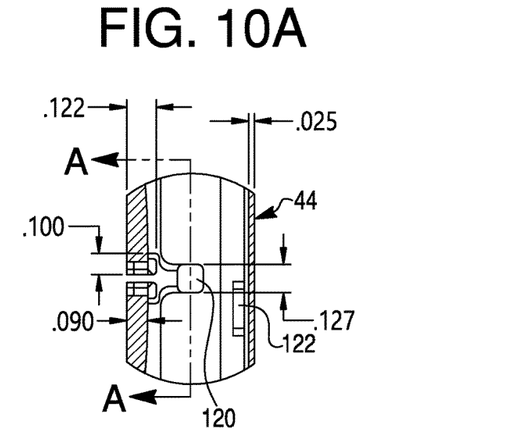
FIGS. 10A and 10B show features of the flexible-membrane sleeve in the region indicated at C in FIG. 9B (10A), and viewed along cross-sectional line A-A in FIG. 10A (10B)

As seen best in FIG. 10A, which corresponds to the region indicated at C in FIG. 9B, ridge 104 in the sleeve is formed at the inner surface of plate 116 on either side of the slit, and has inwardly projecting thickness of about 30 mils in the embodiment shown. Though not shown in the figures, ridge 104 extends around the periphery of the slit and slit enlargement, providing additional structural reinforcement to the slit, to help the slit maintain its shape and dimensions during tissue acquisition.

As can be appreciated from FIGS. 8A-8C, sleeve 44 is stretched laterally and compressed vertically as device 22 is moved from its low-profile to its fully expanded position. To prevent the sleeve from becoming dislodged or moved with respect to the device during operation, the sleeve has a number of structural features designed to interact with slots or projections in device 22, to anchor the sleeve on the device. With reference to FIG. 9B, one of these features is a pin or nubbin 118 formed on the inner distal end of the sleeve, and intended to be received in a cavity 61 formed in the distal end of the device, as seen in FIGS. 4B and 5. Another feature is a pair of pins or nubbins 120 projecting inwardly from opposite sides of the sleeve on either side of slit 102. One of the nubbins is seen face on in the FIGS. 9B and 10A cross sections, and in side sectional view in FIG. 10B, taken along the section line in FIG. 10A. These two nubbins are positioned to be received in a slot formed at the elbow in each arm assembly. Also as seen in FIG. 10A, a ring 122 formed on the back interior surface of the sleeve, immediately below the slit line, is designed to receive a projection 81 on the spreader arm to provide sleeve anchorage to the spreader arm during tissue acquisition. Finally, the rear surface of section 108 has a tapered, enlarged-thickness reinforcing plate 124 with an annular groove 126 formed therein, for receiving a ring at the proximal end of the device, to help resist vertical movement of the sleeve on the device during operation.

Figure 10B:
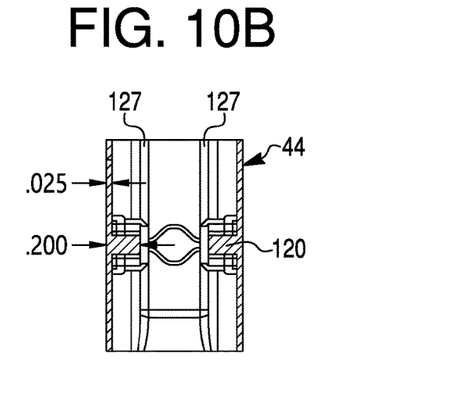

Completing the description of what is shown in FIGS. 9 and 10, the sleeve has a pair of slots 127 formed along opposite interior sides of the sleeve, between proximal and distal sleeve sections 110, 112. The slots ensure that the vacuum applied to the proximal section of the sleeve during tissue acquisition is also transmitted to the distal section of the sleeve, even if a tissue fold drawn into the tissue chamber completely fills the chamber cross section.

The just-described sleeve is formed, e.g., by conventional molding, of an elastic, biocompatible material, such as silicon or other elastic polymer material. One preferred material is silicon having a durometer hardness of Shore A30±5 and a membrane thickness, other than in its reinforced regions, of between 10-50 mils.

D. Operation of the Improved Tissue-Acquisition Device.

One example of a method for using the system 20 will next be described in the context of formation of plications in stomach wall tissue, with particular reference to FIGS. 11-14.

As an initial step, endoscopic guide tube 38 (FIG. 2) is advanced into the stomach via the mouth and esophagus. The endoscope 36 is inserted into the endoscope channel in the stapler handle (not shown) and advanced down the lumen of the stapler handle. The tissue-acquisition device and endoscope are simultaneously passed through the endoscopic guide tube towards the stomach. Once the device and endoscope reach the gastroesophageal junction region of the stomach, the position of the stapler is maintained while the endoscope is advanced further into the stomach.

Figure 11:
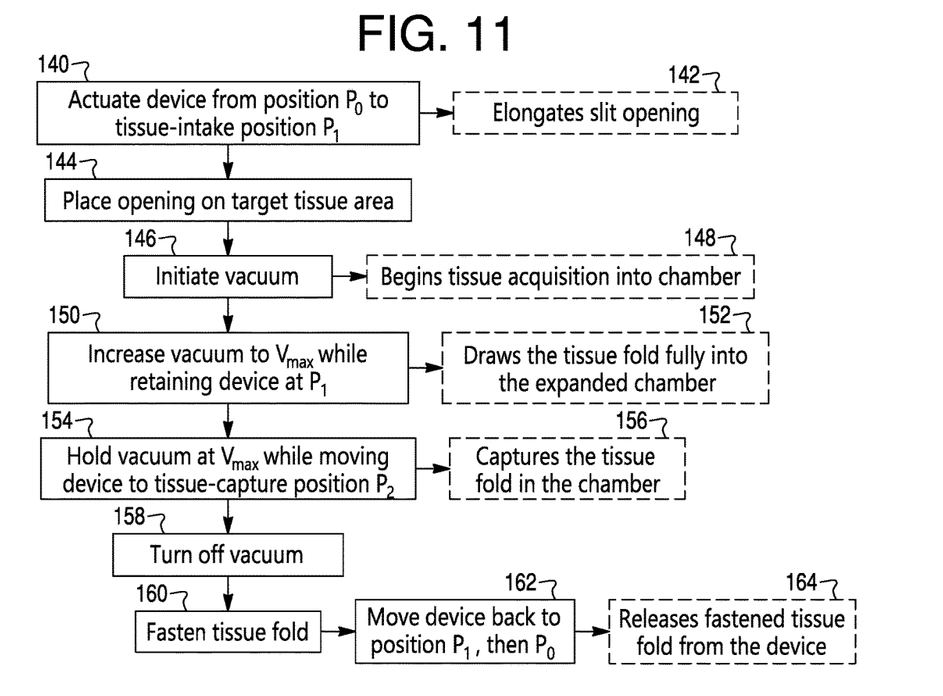
FIG. 11 is a flow chart of the operation of the system in acquiring and fastening a tissue fold, in accordance with one embodiment of the invention.

The device is then advanced to the desired depth and location in the stomach, using articulation controls on the stapler handle, to place slit 102 in the device near the target tissue. To begin tissue acquisition, the drive mechanism in the device, e.g., the hydraulic piston in device 22, is activated, initiating the various device axial and lateral movements described in Section I above. With reference to FIG. 11, the exemplified device is actuated to move the staple and anvil members in the device from their low-profile position $P_o$ shown FIG. 4A to a tissue-intake position $P_1$ at which the two members are close to, but not at, their ultimate tissue-acquisition position shown in FIG. 4C. This step is indicated at 140 in FIG. 11, and results in the elongation of the slit forming the chamber opening, as indicated at 142. The plot in FIG. 12 shows the change in spacing D between the confronting faces of the stapler and anvil members in the device as the device moves from $P_0$ to $P_1$, over the time period $t_0$ to $t_1$.

With the device in its tissue-intake position $P_1$, the opening in the device is now placed by the physician against the region targeted for tissue acquisition, as indicated at 144 in FIG. 11. Once positioned, at time $t_2$ in FIG. 12, the system vacuum is initiated, as indicated at 146 in FIG. 11, beginning tissue acquisition into the chamber, as indicated at 148 in FIG. 11. In the embodiment shown, the vacuum is applied to the tissue chamber so as to increase gradually from $V_0$ to $V_{max}$ over a given time interval $t_2$ to $t_3$, typically 1-3 seconds, as indicated at 150 in FIG. 11, allowing tissue to be drawn into the chamber gradually, thus preventing abrupt stresses on the opening that might otherwise draw sleeves portions around the opening into the chamber along with the tissue. Once $V_{max}$ is reached, at $t_3$ in FIG. 12, tissue continues to fill the chamber, until the tissue fold is fully drawn into the chamber at $t_4$, and as indicated 152 in FIG. 11.

The gradual increase in vacuum to the tissue chamber is provided by a controller operatively connecting the vacuum source in the system to the tissue chamber. In the system described with reference to FIG. 2, the controller function is carried out by reservoir 34, which acts as a storage capacitor, forming and releasing a vacuum slowly as a vacuum is applied to and released from the reservoir. It will be appreciated that the controller may alternatively be an electronically controlled valve or the like, which moves from a fully closed to fully opened condition over a given time period to $t_2$ to $t_3$, e.g., 1-3 seconds.

Figure 12:
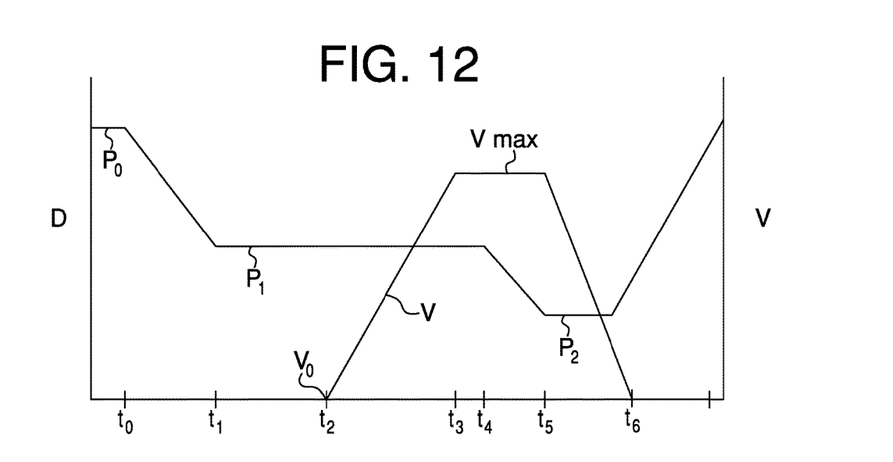
FIG. 12 is a plot showing the changes in device position (D) and applied vacuum (V) during the tissue-acquisition steps in the flow diagram in FIG. 11.

Once the tissue fold is fully formed, at $t_4$ in FIG. 12, and with full vacuum maintained to the chamber, the device is actuated to move to its tissue-capture position $P_2$), indicated at 154 in FIG. 11, and shown in the plot in FIG. 12. At this position, the tissue fold in the chamber is squeezed somewhat between the staples and anvil members' faces, thus securing it within the chamber, as indicated at 156 in FIG. 11. The vacuum is now turned off, as indicated at 158 in FIG.

11, at time $t_5$ in FIG. 12, and begins a gradual decline to $V_0$ (FIG. 12). At the same time, the captured tissue fold may be fastened, e.g., by stapling, as indicated at 160 in FIG. 11. Finally, the device is be moved back to its position $P_1$, then $P_0$, as indicated at 162 in FIG. 11, and the fastened tissue fold is released at time $t_6$ as the chamber vacuum is released, as indicated at 164.

The above-described timing and control of the vacuum, relative to the mechanical positions of the device during operation, have been found to provide two important benefits in tissue acquisition in the present invention: first, there is a significantly reduced tendency of sleeve material around the slit to be drawn into the chamber; secondly, the chamber tends to be more completely and uniformly filled, i.e., a larger, more symmetrical tissue fold is formed.

At the same time, the horizontal slit configuration of the present invention has been found to largely solve the problem of secondary tissue folds being drawn into in the tissue chamber. The basis for this improvement can be seen from FIGS. 13A-13C, which illustrate acquisition of a two-layer tissue fold into the device of the present invention. In these figures, which are similar to FIGS. 7D-7F, sleeve 44 is shown in vertical cross-section in FIG. 4C, and defines a tissue chamber 126, where slit 102 in the device is indicated by gap 128 in FIG. 13A. The figures show the sleeve slit placed against a target layer of tissue 130, e.g., a layer of stomach tissue, which itself is in contact with secondary layer of tissue 132, e.g., an organ or tissue layer that is pressed against the layer of target stomach tissue.

Figure 13A:
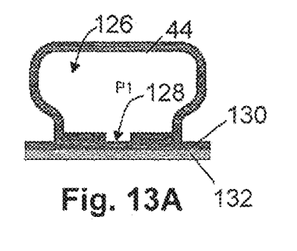
FIGS. 13A-13C illustrate tissue intake into a chamber having a small tissue window in accordance with the present invention, where a secondary layer of tissue spans the entire window.
Figure 13B:
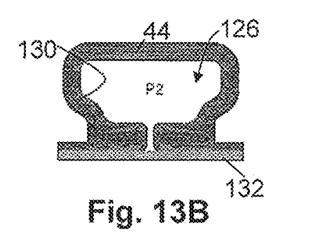
Figure 13C:
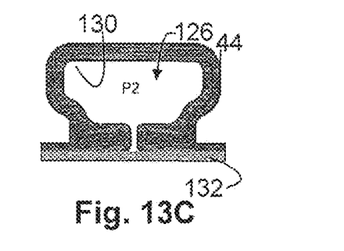

FIG. 13B shows the device after activation to acquire a tissue fold from layer 130, by lowering the chamber pressure from P1 to P2 in the figures. As seen in FIGS. 13B and 13C, the tissue fold has largely closed the gap in slit 102, preventing additional tissue material in layer 132 from entering the chamber, even though the tissue acquisition has produced a pressure differential P2-P1 across the layer.

Figure 14:
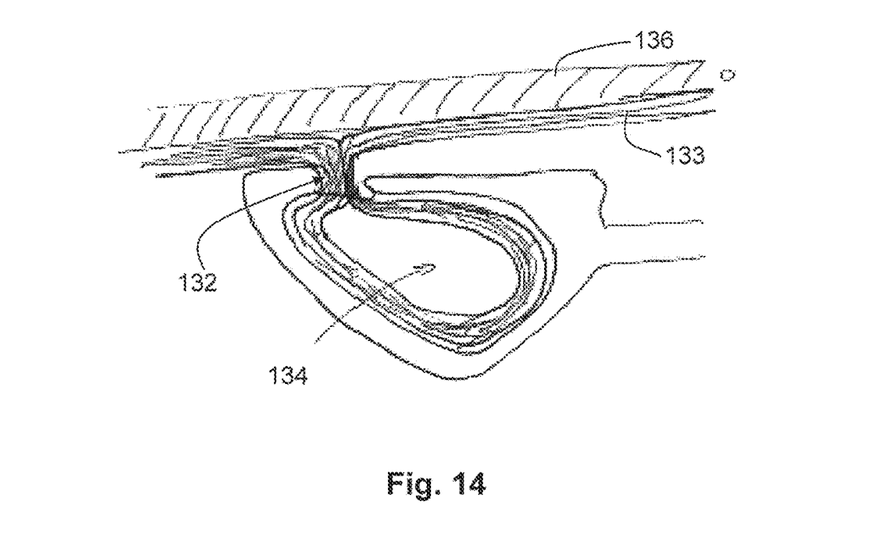
FIG. 14 illustrates the intake of a tissue fold into a tissue chamber in accordance with the present invention.

FIG. 14 is illustrates the same events in tissue acquisition, but in a less schematic form, and where the gap in the sleeve slit, indicated at 132, forces the fold layers in a first into tissue layer into contact with one another as the folded tissue 133 is drawn into the device's tissue chamber, indicated at 134. Here a secondary layer of tissue 136 disposed over layer 133 is prevented from being drawn into the chamber both lack of a gap in the sleeve slit, and because the tissue-fold layers, when completely filling the slit gap, do not transmit the pressure differential across the gap to tissue layer 136.

Once a tissue fold has been formed and captured, the device may be further activated to fasten the tissue fold layers, e.g., by stapling, as described in the above-cited co-owned U.S. patents.

The disclosed systems provide convenient embodiments for carrying out the disclosed compression and stapling functions. However, there are many other widely varying instruments or systems may alternatively be used within the scope of the present invention, Moreover, features of the disclosed embodiments may be combined with one another and with other features in varying ways to produce additional embodiments. Thus, the embodiments described herein should be treated as representative examples of systems useful for forming endoscopic tissue plications, and should not be used to limit the scope of the claimed invention.

Any and all patents, patent applications and printed publications referred to above, including those relied upon for purposes of priority, are incorporated herein by reference.

It is claimed:

1. A device for forming a tissue fold, comprising:
a tissue chamber; and
a flexible-membrane sleeve that covers the tissue chamber, wherein the flexible-membrane sleeve includes an opening having a length in a lateral direction relative to a longitudinal axis of the device that is greater than a width in a direction along the longitudinal axis of the device when the flexible-membrane sleeve is in a relaxed state,
wherein the device is configured to apply a vacuum to the tissue chamber to draw tissue through the opening and into the tissue chamber, and
wherein the device is configured to stretch the opening in the lateral direction during application of vacuum to the tissue chamber.

2. The device of claim 1, wherein the opening is dimensioned to maintain two layers of the tissue fold in contact with one another as they are being drawn into the tissue chamber through the opening.

3. The device of claim 2, wherein said opening, in the relaxed state of the sleeve, includes a width of between 40 and 125 mils.

4. The device of claim 1, wherein the width of the opening remains dimensioned to restrict intake through the opening of additional tissue layers, once the tissue fold has been drawn into the tissue chamber through the opening as the opening is stretched in the lateral direction.

5. The device of claim 1, wherein the opening has a lateral dimension in the relaxed state of between about 10-15 mm, and in a fully elongated state, between 25-50 mm.

6. The device of claim 1, wherein said sleeve includes silicon having a durometer hardness of Shore A30±5 and a membrane thickness of between 10-50 mils.

7. The device of claim 1, wherein said sleeve has a reinforcing lip about the opening to aid in supporting the opening as tissue is being drawn through the opening under the vacuum.

8. The device of claim 1, wherein the tissue chamber is defined by (i) confronting faces of proximal and distal members that are operable to move toward and away from one another along the longitudinal axis, (ii) arm assemblies connecting the proximal and distal members and that expand outwardly, along a second axis substantially perpendicular to the longitudinal axis, as the proximal and distal members move toward one another to a tissue-capture position, and (iii) the flexible-membrane sleeve covering at least portions of said proximal and distal members and having an intermediate portion covering said chamber, and wherein the opening in the sleeve is elongated in the direction of said second axis, such that movement of the arm assemblies outwardly, as the proximal and distal members are moved toward one another, acts to stretch said opening in the lateral direction.

9. The device of claim 8, wherein said sleeve includes reinforcing plates disposed on either side of said opening to resist forces on the slit in a direction of tissue intake.

10. The device of claim 8, wherein an interior surface of said sleeve has one or more slots extending between proximal and distal regions of the device to maintain a vacuum connection within the chamber as the tissue fold presses against said interior surface during acquisition of the tissue fold.

11. The device of claim 8, wherein at least one arm assembly includes an elbow that defines a slot, and an interior surface of the sleeve includes a protrusion that is received in the slot.

12. The device of claim 8, wherein at least one of the proximal or distal members includes a staple cartridge and a staple driver in a first housing, and the other of the proximal or distal members includes a staple anvil in a second housing.

13. The device of claim 1, which further includes a reservoir connecting the tissue chamber in the device to a vacuum source, for modulating the rate at which vacuum is applied to the tissue chamber from the vacuum source.

14. A method for forming a tissue fold, comprising:
    (a) placing a device against tissue, wherein the device includes a staple member, an anvil member, and a flexible-membrane sleeve, and wherein the flexible-membrane sleeve includes an elongated opening; and
    (b) applying a vacuum to a chamber defined by the staple member, the anvil member, and the flexible-membrane sleeve, wherein the vacuum is controlled relative to a distance between the staple member and the anvil member as tissue is being drawn through the opening into the chamber, and wherein a maximum vacuum in the chamber is reached before the elongated opening has been fully stretched.

15. The method of claim 14, wherein the opening is elongated in a lateral direction relative to a longitudinal axis of the device.

16. The method of claim 14, wherein the elongated opening, in a relaxed state of the sleeve, includes a width of between 20 and 125 mils.

17. The method of claim 14, which further includes, during applying step (b), stretching the elongated opening in a lateral direction.

18. The method of claim 14, wherein step (b) is carried out by applying a vacuum to a reservoir bottle that is connected to said chamber.

19. An apparatus for forming a tissue fold, comprising
    (a) a device having a tissue chamber covered by a flexible-membrane sleeve, said sleeve having an opening having a length in a lateral direction relative to a longitudinal axis of the device that is greater than a width in a direction along the longitudinal axis of the device when the flexible-membrane sleeve is in a relaxed state, the device further including a staple cartridge and an anvil movable relative to each other along the longitudinal axis;
    (b) a vacuum source for applying vacuum to said chamber; and
    (c) a controller operatively connected to said vacuum source for controlling the vacuum applied to said chamber, to control the rate at which tissue is drawn into said chamber.

20. The apparatus of claim 19, wherein the opening is dimensioned to maintain two layers of the tissue fold in contact with one another as they are being drawn into the tissue chamber through the opening.

21. The apparatus of claim 20, wherein the opening has a width, in the relaxed state of the sleeve, of between 40 and 125 mils.

22. The apparatus of claim 19, wherein said controller includes a reservoir operatively connecting the vacuum source to the chamber.

23. The apparatus of claim 19, wherein said device operates to stretch the opening in the lateral direction as the controller is controlling a rate of vacuum being formed in said chamber.

24. The apparatus of claim 23, wherein the tissue chamber is defined by (i) confronting faces of proximal and distal members that are operable to move toward and away from one another along the longitudinal axis, (ii) arm assemblies connecting the proximal and distal members and that expand outwardly, along a second axis substantially perpendicular to the longitudinal axis, as the proximal and distal members move toward one another to a tissue-capture position, and (iii) the flexible-membrane sleeve covering at least portions of said proximal and distal members and having an intermediate portion covering said chamber, and wherein the opening in the sleeve is elongated in the direction of said second axis, such that movement of the arm assemblies outwardly, as the proximal and distal members are moved toward one another, acts to stretch said opening in the lateral direction.

25. The apparatus of claim 24, wherein said sleeve includes reinforcing plates disposed on either side of said opening to resist forces on the slit in the direction of tissue intake.

26. The apparatus of claim 24, wherein an interior surface of said sleeve has one or more slots extending between proximal and distal regions of the device to maintain a vacuum connection within the chamber as the tissue fold presses against said interior surface during acquisition of the tissue fold.

27. The apparatus of claim 24, wherein at least one arm assembly includes an elbow that defines a slot, and an interior surface of the sleeve includes a protrusion that is received in the slot.

28. The apparatus of claim 24, wherein at least one of the proximal or distal members includes the staple cartridge and a staple driver in a first housing, and the other of the proximal or distal members includes the anvil in a second housing.

29. The apparatus of claim 19, wherein said controller is configured to control the vacuum relative to a distance between the staple cartridge and the anvil.

\* \* \* \* \*